(12) United States Patent
Llorens et al.

(10) Patent No.: US 8,162,868 B2
(45) Date of Patent: Apr. 24, 2012

(54) ARCH SUPPORT WRAP

(76) Inventors: Steve Llorens, New York, NY (US);
Maria Marcial, New York, NY (US)

(*) Notice: Subject to any disclaimer, the term of this patent is extended or adjusted under 35 U.S.C. 154(b) by 158 days.

(21) Appl. No.: 12/539,456

(22) Filed: Aug. 11, 2009

(65) Prior Publication Data

US 2010/0249685 A1   Sep. 30, 2010

(51) Int. Cl.
*A61F 5/00* (2006.01)
*A43B 7/22* (2006.01)

(52) U.S. Cl. .............................. 602/28; 36/91

(58) Field of Classification Search ............... 36/44, 91, 36/43, 88, 10, 71, 100, 101, 159–161, 163–164, 36/174, 180–181, 155; 128/581, 586, 602, 128/604, 846, 869, 882; 602/28, 23, 5, 1
See application file for complete search history.

(56) References Cited

U.S. PATENT DOCUMENTS

| | | | |
|---|---|---|---|
| 1,267,796 A | 5/1918 | Pakas | |
| 1,492,514 A | 4/1924 | Jensen | |
| 1,577,203 A | 3/1926 | Cramer | |
| 2,454,836 A | 11/1948 | Rayner | |
| 2,633,130 A | 3/1953 | Scholl | |
| 2,917,849 A * | 12/1959 | Scholl | 36/180 |
| 4,109,661 A * | 8/1978 | Fukuoka | 36/141 |
| 4,271,605 A | 6/1981 | Raczka | |
| 4,392,487 A | 7/1983 | Selner et al. | |
| 4,510,699 A | 4/1985 | Nakamura | |
| 5,473,781 A | 12/1995 | Greenberg | |
| D380,267 S | 6/1997 | Roth | |
| D380,290 S | 7/1997 | Nakagawa | |
| 5,840,053 A | 11/1998 | Roth | |
| 2005/0251073 A1 | 11/2005 | Roth | |
| 2007/0283597 A1* | 12/2007 | Logan | 36/91 |

FOREIGN PATENT DOCUMENTS

| | | |
|---|---|---|
| EP | 0786978 | 4/1996 |
| WO | WO9611651 | 4/1996 |

* cited by examiner

*Primary Examiner* — Patricia Bianco
*Assistant Examiner* — Tarla Patel
(74) *Attorney, Agent, or Firm* — C. Rachal Winger; K&L Gates LLP

(57) ABSTRACT

An orthopedic device to provide support and cushioning to the foot to alleviate plantar fasciitis, fallen arches, heel pain, bunions, and other conditions.

19 Claims, 4 Drawing Sheets

ARCH SUPPORT WRAP

BACKGROUND

1. Field of the Invention

The present device relates to the field of orthopedic support devices, particularly arch supports for feet.

2. Background

Many people suffer from foot and related leg and back pain due to a lack of proper support in the arches of the feet. So-called "flat feet" or "fallen arches" can result from genetic predisposition, wearing improper footwear, or injuries. When the arches of the feet are not in their proper position, the bones of the feet, ankles, legs, knees, hips, and even the spine may also fall out of alignment. This can place strain on the supportive muscle, tendon, and ligament structures, as well as cause bones to rub against each other, which can result in pain.

Several over-the-counter arch supports and supportive insoles presently exist. However, a person may have to try many different types of commercial arch supports or insoles before finding a pair that fits properly and works, which can be expensive and time-consuming. Custom-fit orthotics are also available, and although the fit and function of these are often superior to that of over-the-counter devices, they are much more expensive.

Although these devices can provide relief by properly supporting the arches, a person either has to purchase multiple pairs of supports for placement in more than one pair of shoes, or continually switch the devices between pairs of shoes. With custom orthotics, purchasing multiple devices can be especially expensive. Therefore, a person must pay a premium for the convenience of not having to move a single pair of supports between shoes.

Wraps can work in conjunction with shoes and socks to provide more support and cushioning to the foot. Wraps to support the ankle joint and the arch by augmenting the ligament and tendon structures exist. Most arch wraps work by providing compression to support the plantar fascia and alleviate excess tension on it. However, they do not provide specifically for a solid arch support underneath the arches of the feet, which can also help to properly align the foot itself, or for any cushioning.

Such supports and wraps are typically designed to alleviate only one type of condition, such as plantar fasciitis, fallen longitudinal arches, fallen metatarsal arches, or heel pain. Different conditions require different configurations of wraps and supports. As a result a person must purchase a device specific to a particular condition, which may not be of use to alleviate other types of foot pain.

What is needed is a wrap that can provide an optionally interchangeable arch support, additional cushioning to the foot, and can be used for multiple conditions.

DETAILED DESCRIPTION

Figure 1:
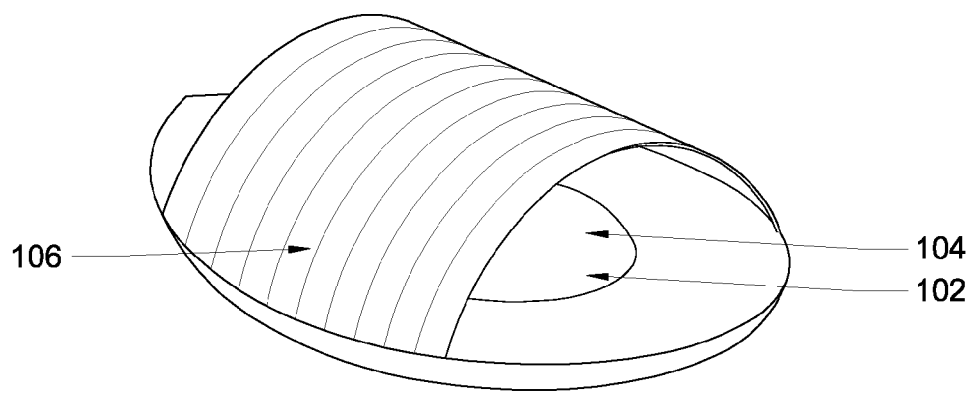
FIG. 1 depicts a perspective view of an embodiment of the present device.

FIG. 1 depicts a perspective view of an embodiment of the present device. In some embodiments, a base member 102 can have a raised region 104 located substantially in its center. At least one elongated member 106 can extend substantially perpendicularly or any other known and/or convenient angle from at least one lateral edge of a base member 102.

Figure 1A:
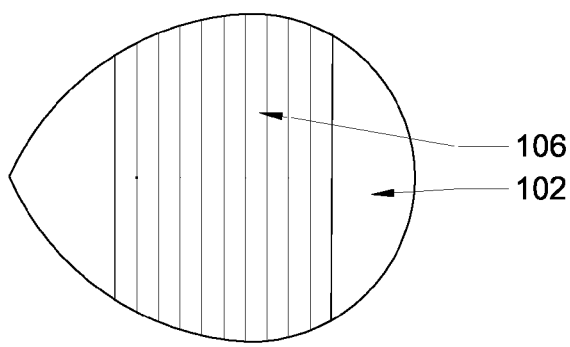
FIG. 1a depicts a top view of an embodiment of the present device.

As shown in FIG. 1a, a base member 102 can have a substantially ovoid geometry, having one end substantially rounded and the opposite end tapered to a point. However, in other embodiments, a base member can have any known and/or convenient geometry. A base member 102 can be solid or, in other embodiments, perforated.

In some embodiments, a base member 102 can be comprised of a single piece of one material, but in other embodiments, as shown in FIG. 1a, can be comprised of at least two layers of the same or different materials. A base member 102 can be comprised of an elastomeric material, polymer, textile, or any other known and/or convenient material. In embodiments having two layers, a top layer 108 and a bottom layer 110 can each be made of an elastomeric material, neoprene, rubber, polymer, or any other known and/or convenient material. In some embodiments, a base member 102 can be further comprised of wicking, insulating, antimicrobial, and/or quick-drying materials. In some embodiments, a base member can be comprised of a thermally stable material capable of maintaining a desired temperature for a given length of time, in order to provide heat or cold to an affected area.

Figure 1B:
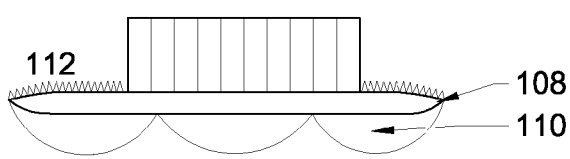
FIG. 1b depicts a side view of an embodiment of the present device.

In some embodiments, as shown in FIG. 1b, a top layer 108 can have its top surface covered with an additional layer 112 of a textile, polymer, or any other known and/or convenient material. In some embodiments, this layer 112 can be of a material having a soft texture or wicking properties to improve comfort. In some embodiments, a bottom layer 110 can have a no-slip texture on its bottom surface 114, such as, but not limited to that of neoprene or other rubberized material.

Figure 1C:
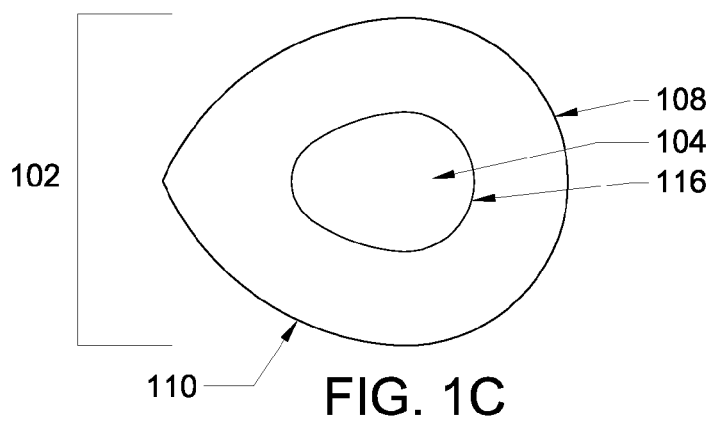
FIG. 1c depicts a bottom view of an embodiment of the present device.

In some embodiments, as shown in FIG. 1c, a raised region 104 can have a substantially ovoid shape, but in other embodiments can have any other known and/or convenient geometry. In some embodiments, a raised region 104 can be delineated by stitching 116, but in other embodiments can be delineated by a heat weld, ultrasonic weld, or any other known and/or convenient method. As shown in FIG. 1c, a raised region 104 can protrude from the top surface of a top layer 108, the bottom surface of a bottom layer 110, or both a top layer 108 and a bottom layer 110. A raised region 104 can enhance support and improve comfort by providing a space between a base member 102 and a user's foot to promote air circulation.

Figure 2:
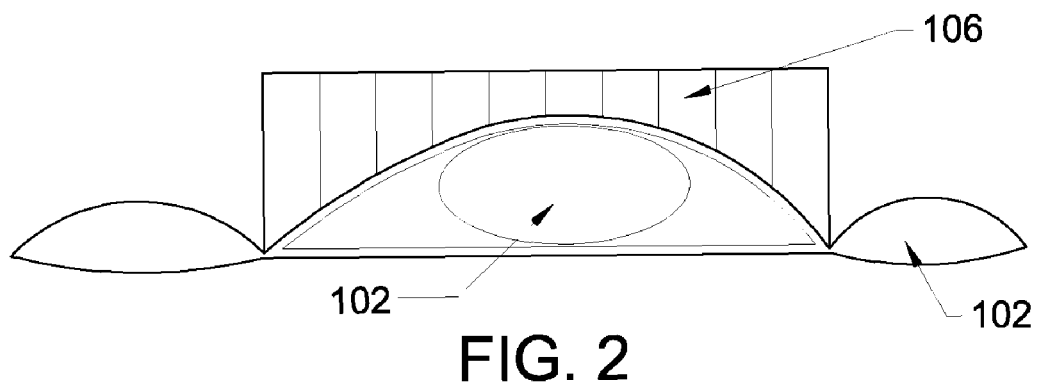
FIG. 2 depicts a cutaway side view of an embodiment of the present device.
Figure 2A:
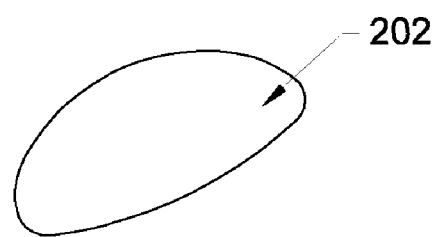
FIG. 2a depicts a detail view of an embodiment of a support member of the present device.

In some embodiments, a raised region 104 can be comprised of only a base member 102, but in other embodiments, as shown in FIG. 2, can be further comprised of a support member 202. In some embodiments, as shown in FIG. 2a, a support member 202 can have a substantially ovoid shape, but in other embodiments can have any other known and/or convenient geometry. A support member 202 can be comprised of an elastomeric material, rubber, polymer, cotton, gel, or any other known and/or convenient material. In other embodiments, a support member 202 can be a bladder that can be filled with air, water, gel, or any other known and/or convenient material in either a fixed or a variable quantity. Material comprising a support member 202 can be selected to provide desired levels of firmness for support. A support member 202 can also come in a variety of sizes to accommodate different size feet and different levels of desired support. A support member 202 can also be comprised a thermally stable material capable of retaining heat or cold for a given length of time in order to provide hot or cold therapy to an affected area.

Figure 3:
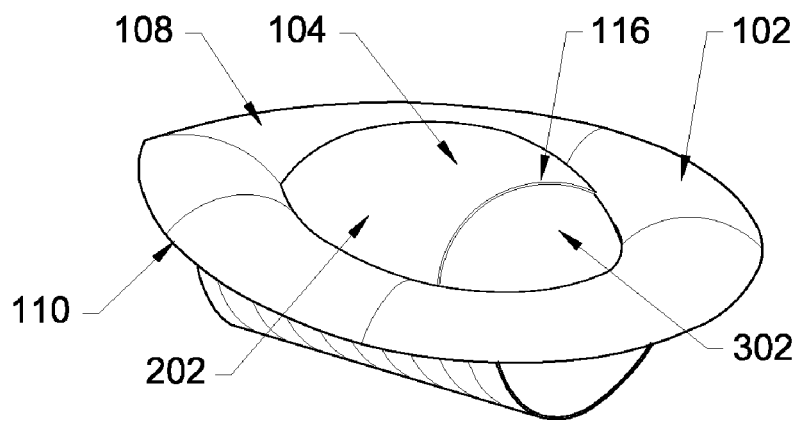
FIG. 3 depicts a perspective view of another embodiment of the present device.

As shown in FIG. 3, in some embodiments, a raised region 104 can further comprise a pocket 302 in either the top layer 108 or bottom layer 110, or between these layers, of a base member 102. In such embodiments, a support member 202 can be removable and interchangeable with an alternative support member 202 of a different size or firmness.

In some embodiments, as shown in FIG. 1, at least one flexible, elongated member 106 can extend substantially perpendicularly from at least one lateral edge of a base member 102, or in any other known and/or convenient orientation. As shown in FIG. 1, in some embodiments, a single flexible, elongated member 106 can have one end attached to one lateral edge of a base member 102 and the other end attached to the opposite lateral edge of a base member 102. In some embodiments, the ends of a flexible, elongated member 106 can be joined to a base member 102 by stitching, adhesive, heat weld, or any other known and/or convenient method.

In some embodiments, a flexible, elongated member 106 can be comprised of an elastomeric material, but in other embodiments can be made from any other known and/or convenient material. Further, a flexible, elongated member 106 can be comprised of an elastomeric material having a unidirectional stretch that can be oriented along the longitudinal axis of a flexible, elongated member.

Figure 4:
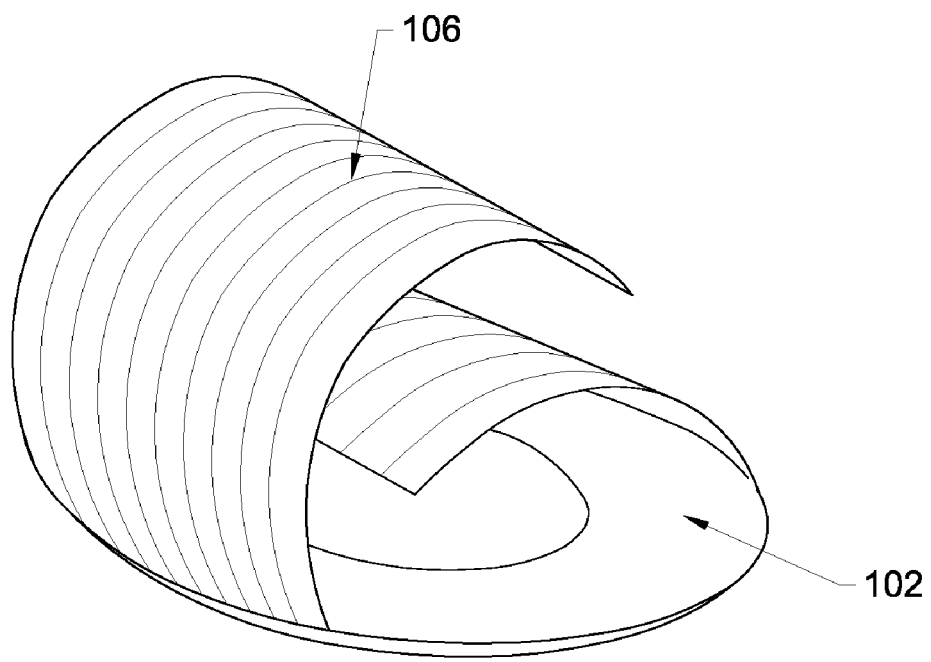
FIG. 4 depicts a perspective view of another embodiment of the present device.
Figure 5:
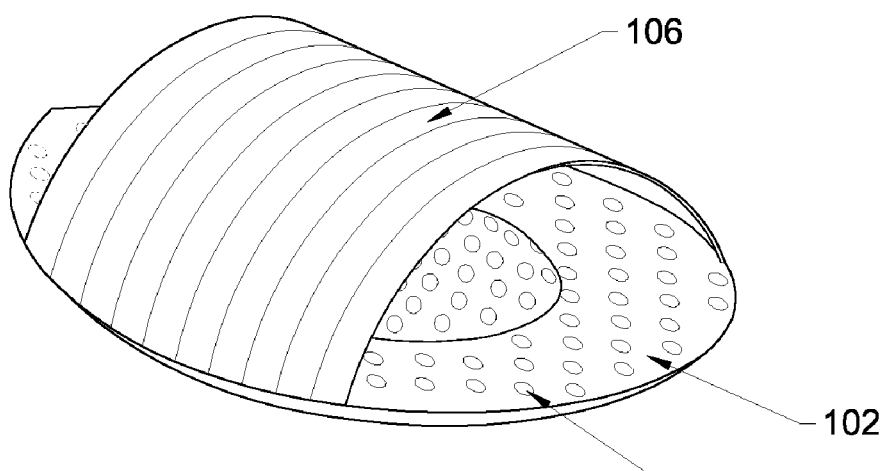
FIG. 5 depicts a perspective view of another embodiment of the present device.

In embodiments having a pair of flexible elongated members 106, as shown in FIG. 4, the distal ends of flexible, elongated members 106 can further comprise complementary parts of hook-and-loop material, snaps, hooks, or any other known and/or convenient closure device. In other embodiments, as shown in FIG. 5, a single flexible, elongated member 106 can extend from either lateral edge of a base member 102 and connect to another region on the surface of a base member 102 by hook-and-loop material, snaps, hooks, or any other known and/or convenient closure device. In other embodiments, a single flexible, elongated member 106 can extend from one edge of a base member 102 and be affixed to either an opposite edge or any other known and/or convenient location on a base member 102. In some embodiments, flexible, elongated member or members 106 can be of length sufficient to wrap around the arch or instep portion of a foot. In other embodiments, flexible, elongated member or members 106 can be longer and positioned in any known and/or convenient place on a base member 102 such that flexible, elongated member or members 106 can wrap around an ankle or other part of a foot to provide further support.

FIG. 5 depicts another embodiment of the present device in which a base member can have a plurality of perforations 502. These perforations can promote air circulation and improve comfort.

Figure 6:
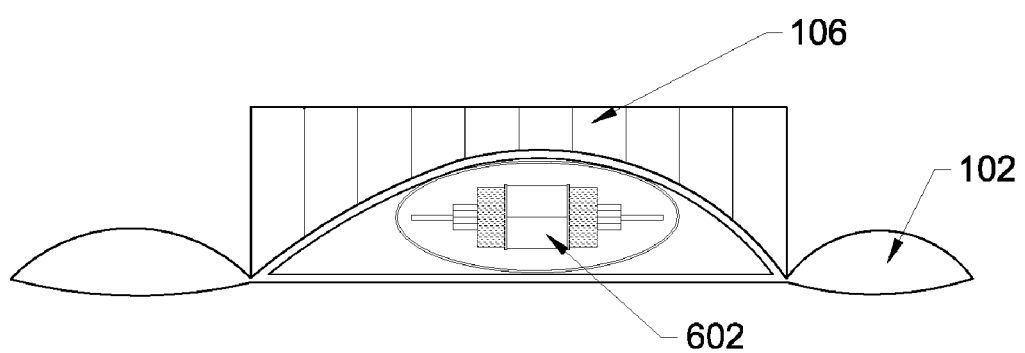
FIG. 6 depicts a cutaway perspective view of another embodiment of the present device.

FIG. 6 depicts another embodiment of the present device in which an oscillating device 602 can be located in a base member 102. In some embodiments, an oscillating device 602 can be removable or interchangeable, but in other embodiments can be permanently fixed within a base member 102.

In use, a person places the present device underneath the sole of a foot, positioning a base member 102 and a raised region 104 substantially under an area of a foot needing support or cushioning. A user can position the present device under the longitudinal arch, metatarsal arch, heel, or in any other desired position to alleviate discomfort or provide support. At least one flexible, elongated member 106 can wrap around a foot to secure the present device in place on a foot, as well as provide additional compression and support. If a user changes shoes, he can do so without having to change a support device between pairs of shoes.

In embodiments having a removable support member 202, a person can select a support member 202 based on the desired level of support, and then insert a support member 202 into a pocket 302. A user can position the present device under the longitudinal arch, metatarsal arch, heel, or in any other desired position to alleviate discomfort or provide support.

Although the invention has been described in conjunction with specific embodiments thereof, it is evident that many alternatives, modifications and variations will be apparent to those skilled in the art. Accordingly, the invention as described and hereinafter claimed is intended to embrace all such alternatives, modifications and variations that fall within the spirit and broad scope of the appended claims.

What is claimed is:

1. An orthopedic support device, comprising: a base member having a modified, substantially rectangular geometry with opposite ends and a first lateral edge substantially symmetrical to a second lateral edge, wherein the first lateral edge of said base member is of a length less than that of said second lateral edge, and said opposite ends are substantially symmetrically curved to extend past the length of said first lateral edge to create a maximum base member length located at a point located at less than substantially a half of the length between said first and second lateral edges and taper to substantially meet the ends of said second lateral edge;

a raised region substantially in the center of said base member; a support member positioned within said raised region; at least one flexible, elongated member having a first end and a second end, the first end attaching to and extending substantially perpendicularly from one lateral edge of said base member and the second end attaching to and extending substantially perpendicularly from the opposite lateral edge of said base member wherein said base member further comprises a bottom layer having an upper surface and a lower surface; a top layer having an upper surface and a lower surface; wherein said bottom layer is mated to said top layer such that said support member is positioned between said layers within said raised region; and the ends of said flexible, elongated member are inserted between said layers and wherein said elongated member removably secures the device to a user's foot such that said device can be worn independently of shoes and with more than one pair of shoes.

2. The device of claim 1, wherein said elongated member is comprised of an elastomeric material.

3. The device of claim 1, wherein said top layer and said bottom layer of said base member are comprised of a material selected from the group consisting of: neoprene, rubber, polymer, elastomer, cotton, synthetic fiber.

4. The device of claim 1, further comprising a textile covering on the upper surface of said top layer and a non-skid texture on the lower surface of said bottom layer.

5. The device of claim 4, wherein said textile covering is comprised of a material selected from the group consisting of: cotton, synthetic fiber, polypropylene.

6. The device of claim 5, wherein said support member is comprised of a material selected from the group consisting of: elastomer, rubber, neoprene, polymer, cotton, synthetic fiber, gel.

7. The device of claim 6, wherein said support member is removable and interchangeable.

8. The device of claim 7, wherein said support member is comprised of a thermally stable material.

9. The device of claim 6, further comprising an oscillating device located within said base member.

10. The device of claim 5, wherein said support member is a bladder filled with material selected from the group consisting of: air, fluid, gel.

11. The device of claim 10, wherein the quantity of material filling said support member is fixed.

12. The device of claim 10, wherein the quantity of material filling said support member is variable.

13. The device of claim 10, wherein said support member is removable and interchangeable.

14. The device of claim 1, wherein said base member is perforated.

15. The device of claim 1, wherein said base member is comprised of a thermally stable material.

16. An orthopedic support device, comprising:
a base member having a modified, substantially rectangular geometry with opposite ends and a first lateral edge substantially symmetrical to a second lateral edge, wherein the first lateral edge of said base member is of a length less than that of said second lateral edge, and said opposite ends are substantially symmetrically curved to extend past the length of said first lateral edge to create a maximum base member length located at a point located at less than substantially a half of the length between said first and second lateral edges and taper to substantially meet the ends of said second lateral edge;
a raised region, the base of which having a surface area less than that of said base member and positioned substantially in the center of said base member;
a support member positioned within said raised region;
a first flexible, elongated member, having a first end and a second end, the first end extending substantially perpendicularly from said first lateral edge of said base member and having a substantially uniform width substantially equivalent to the length of said first lateral edge;
a second flexible, elongated member having a first end and a second end, the first end extending substantially perpendicularly from said second lateral edge of said base member and having an initial width substantially equivalent to the length of said second lateral edge, substantially symmetrically curvilinearly tapering to a width less than the length of said second lateral edge at a point substantially halfway along the length of said second elongated member, then substantially symmetrically curving inward so that the distal portion of said elongated member is of a substantially uniform width substantially equivalent to approximately one-third the length of said lateral edge, each second end of each flexible, elongated member having components of an attachment device to selective connect said second ends, and wherein when said device is positioned to longitudinally surround at least a portion of a foot, said flexible elongated members, when connected at the second ends form a closed loop are capable of exerting a compressive force on a foot.

17. The device of claim 16, wherein said base member further comprises:
a bottom layer having an upper surface and a lower surface;
a top layer having an upper surface and a lower surface;
wherein said bottom layer is mated to said top layer such that said support member is positioned between said layers within said raised region.

18. The device of claim 17, wherein attachment device is a hook-and-loop closure.

19. The device of claim 18, wherein said base member and said pair of elongated members are fabricated from materials selected from the group consisting of: elastomer, neoprene, silicone, fabric, latex.

* * * * *